(12) United States Patent
Schlitt et al.

(10) Patent No.: US 7,667,407 B2
(45) Date of Patent: Feb. 23, 2010

(54) ODOR NEUTRALIZING FLUORESCENT SUNLAMP

(75) Inventors: Steven C. Schlitt, Merrimac, MA (US); Keith A. Klinedinst, Hudson, MA (US)

(73) Assignee: OSRAM Sylvania Inc., Danvers, MA (US)

( * ) Notice: Subject to any disclaimer, the term of this patent is extended or adjusted under 35 U.S.C. 154(b) by 309 days.

(21) Appl. No.: 11/891,750

(22) Filed: Aug. 13, 2007

(65) Prior Publication Data

US 2009/0045719 A1    Feb. 19, 2009

(51) Int. Cl.
*H01J 17/16*    (2006.01)
(52) U.S. Cl. .................................. 313/635
(58) Field of Classification Search ............. 313/635, 313/634
See application file for complete search history.

(56) References Cited

U.S. PATENT DOCUMENTS

| 3,987,331 | A | | 10/1976 | Schreurs | 313/486 |
| 5,565,685 | A | * | 10/1996 | Czako et al. | 250/504 R |
| 5,801,483 | A | | 9/1998 | Watanabe et al. | 313/485 |
| 6,387,844 | B1 | * | 5/2002 | Fujishima et al. | 502/350 |
| 6,984,931 | B2 | | 1/2006 | Dutta et al. | 313/487 |
| 2004/0155570 | A1 | * | 8/2004 | Dutta et al. | 313/486 |

* cited by examiner

*Primary Examiner*—Toan Ton
*Assistant Examiner*—Hana A Sanei
(74) *Attorney, Agent, or Firm*—Robert F. Clark

(57) ABSTRACT

A fluorescent tanning lamp having a glass envelope has an ultra-violet light reflecting coating covering at least 180° of an inside surface of the envelope; and a phosphor layer covering substantially 360° of the inside surface of the envelope, including overlying the ultra-violet reflecting coating. An odor reducing photocatalytic material is provided on an outside surface of the envelope, the photocatalytic material being coextensive with the ultra-violet light reflecting material. A preferred material is anatase $TiO_2$; i.e., the crystalline form.

9 Claims, 6 Drawing Sheets

INSTALL LAMP EMITTING UVR IN A MAJOR DIRECTION AND A MINOR DIRECTION

ENERGIZE SAID LAMP TO ACTIVATE PHOTOCATALYST WITH UVR FROM SAID MINOR DIRECTION

Fig. 7

ODOR NEUTRALIZING FLUORESCENT SUNLAMP

TECHNICAL FIELD

This invention relates to lamps and more particularly to fluorescent lamps. Still more particularly, it relates to fluorescent lamps used in tanning booths and to such lamps that supply not only UV radiation but perform a deodorizing function as well.

BACKGROUND ART

Indoor tanning, with the use of ultraviolet emitting fluorescent lamps, has become a popular activity for those persons seeking a tan during seasonal periods when available sunlight is at a minimum or at less predictable levels. An added benefit of indoor tanning, as opposed to outdoor tanning by natural sunlight, is that it affords the possibility to better control the exposure of the skin to UV radiation that potentially can cause sunburn (erythema). Modern tanning equipment is designed to deliver a regulated dose of UV energy that is based on a person's skin type, and the equipment is fitted with a timer to terminate the tanning session when the proper dose has been delivered. In addition, in a professional indoor tanning facility, FDA regulated equipment and lamps are applied by trained personnel who often teach tanners how their particular skin type reacts to ultraviolet radiation and how to avoid sunburn—both outdoors as well as in the salon.

Due to the popularity of indoor tanning, many salons experience a high level of usage of the equipment. And, because of this high level of usage, there is significant concern regarding the hygiene of both the equipment and the general environment to which the clientele are exposed. Since persons lie down on sunbeds to receive the UV radiation (UVR), there is a concern about the transfer of bacteria, germs or other substances from one person to another by contact with contaminated surfaces. Proper sanitation of the acrylic surface of the sunbed is therefore of paramount importance. It is usual practice to clean the acrylic sheet with a bactericidal detergent after each use. The salon attendant may also spray a deodorizing fragrance (air freshener) in the vicinity of the sunbed prior to the arrival of the next client.

In the case of a sunbooth, the tanner stands approximately in the center of a small cabin in which multiple tanning lamps are situated vertically on panels that surround the client. The usual type of UV lamp that is used in this application is of the type known as a Reflector Lamp. This class of lamps maximizes the radiation received by the client by directing and distributing the radiation toward the middle of the booth by means of a reflector that is internal to the lamp. Booths are often fitted with reflective metallic surfaces behind the lamps in order to reflect stray radiation from the back of the lamps and opposing panels back toward the middle of the booth. Such designs effectively integrate the radiation of adjoining and opposing lamps to bathe the tanner with UVR.

These reflector lamps are designed to maximize the radiation received by a user by directing and distributing the radiation towards the middle of the booth by means of a reflector that is internal to each lamp. Ideally, for purposes of maximum tanning efficiency, all of the ultraviolet radiation incident upon the internal reflector would be reflected towards the portion of the lamp wall upon which the reflecting material has not been deposited (i.e., the window). However, it has been found that, on average, about 5 percent of the desired ultraviolet radiation (with wavelength between about 300 nm and about 400 nm) that is emitted by a reflector sunlamp is emitted through the portion of the lamp upon which the reflector has been deposited, that is, in a direction away from the user, and thus is lost.

In a sunbooth, because the client only makes physical contact with the floor (with the feet) and perhaps with support straps or handles (with the hands) at the top of the booth, the necessary cleaning of the booth is minimal as compared with a sunbed. Regardless of the minimal required cleaning, the air within the cabin and the air in the surrounding environment will very likely retain the odors coming from persons who perspire as a natural reaction to higher temperatures frequently realized in indoor tanning equipment. During perspiration, a protein is secreted that is subsequently consumed by bacteria that live in and on the skin, thereby producing a characteristic odor. With a high level of traffic in the suntan parlor, these odors could reach disturbing levels especially to the type of cosmetically conscious people most attracted to indoor tanning.

Additionally, it is known that $TiO_2$ can be used as a photocatalytic agent to remove odors from environmental air. In other cases, devices for air deodorization are described in which the photocatalytic materials are deposited directly onto the surface of a fluorescent lamp. In these cases, however, the fluorescent lamps are either of the type used for general illumination purposes (with the emitted light mainly in the visible range, with wavelengths between approximately 400 and 800 nm) or of the type used for germicidal purposes (with the emitted light mainly in the higher energy ultraviolet range, with wavelengths between approximately 200 and 280 nm). In contrast, fluorescent lamps useful for tanning purposes are designed with the emitted light mainly in the so-called UVA region (320-400 nm) and, to a small degree, in the UVB region (280-320 nm).

Presently, bodily odors that are formed in a tanning salon are not removed. Rather, they are masked. An attendant at the tanning salon usually sprays a fragrance into the area in, and surrounding, a piece of tanning equipment. To some clients this spray may be pleasing; to others this artificial odor of fragrance may be unpleasant. Obviously, to combat odors, a person must proactively work to dispel the odors with a chemical spray. It should also be mentioned that some sprays might contain compounds that, in fact, may be harmful to the health of the customers and salon personnel.

In consideration of the current methods of treating odors in the indoor tanning industry, it is substantially much more advantageous to treat the air in a more passive way.

It would be an advance in the art if a use could be found for this previously unused radiation and further provide a deodorizing function in a tanning booth.

DISCLOSURE OF INVENTION

It is, therefore, an object of the invention to obviate the disadvantages of the prior art.

It is another object of the invention to enhance fluorescent tanning lamps.

Still another object of the invention is the provision of a lamp that can utilize previously unused radiation.

These objects are accomplished, in one aspect of the invention, by a fluorescent tanning lamp having: a glass envelope; an ultra-violet light reflecting coating covering at least 180° of an inside surface of the envelope; and a phosphor layer covering substantially 360° of the inside surface of the envelope, including overlying the ultra-violet reflecting coating, the improvement comprising: a photocatalytic material on an outside surface of the envelope, the photocatalytic material being coextensive with the ultra-violet light reflecting material.

The photocatalytic material, activated by the previously unused ultra-violet radiation, is effective for deodorizing the air within the tanning environment.

BRIEF DESCRIPTION OF THE DRAWINGS

FIG. 7 is a flow diagram of a method of operation.

BEST MODE FOR CARRYING OUT THE INVENTION

Figure 1:
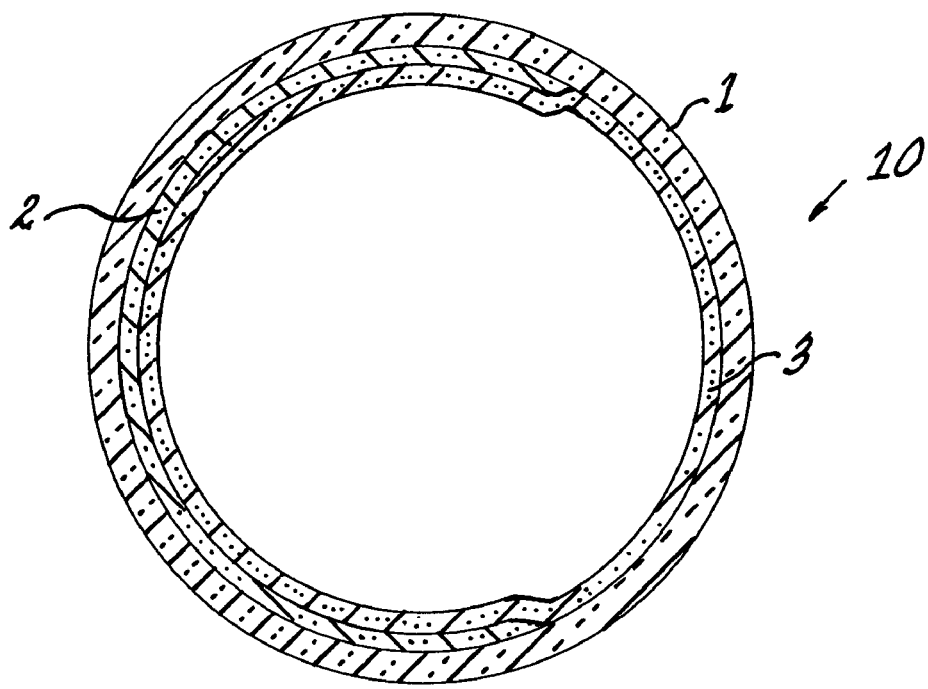
FIG. 1 is a sectional, elevational view of fluorescent sun tanning lamp.

For a better understanding of the present invention, together with other and further objects, advantages and capabilities thereof, reference is made to the following disclosure and appended claims taken in conjunction with the above-described drawings.

Referring now to the drawings with greater particularity, there is shown a cross-sectional view of a fluorescent sun tanning lamp 10 comprised of a glass envelope 1 having a reflector layer 2 covering a portion of the internal surface of the envelope and a phosphor layer 3 overlying the reflector layer. Such lamps are shown in U.S. Pat. No. 3,987,331, which is assigned to the assignee of the present invention (now, by change of name, Osram Sylvania Inc.) and the teachings thereof are incorporated by reference.

Figure 2:
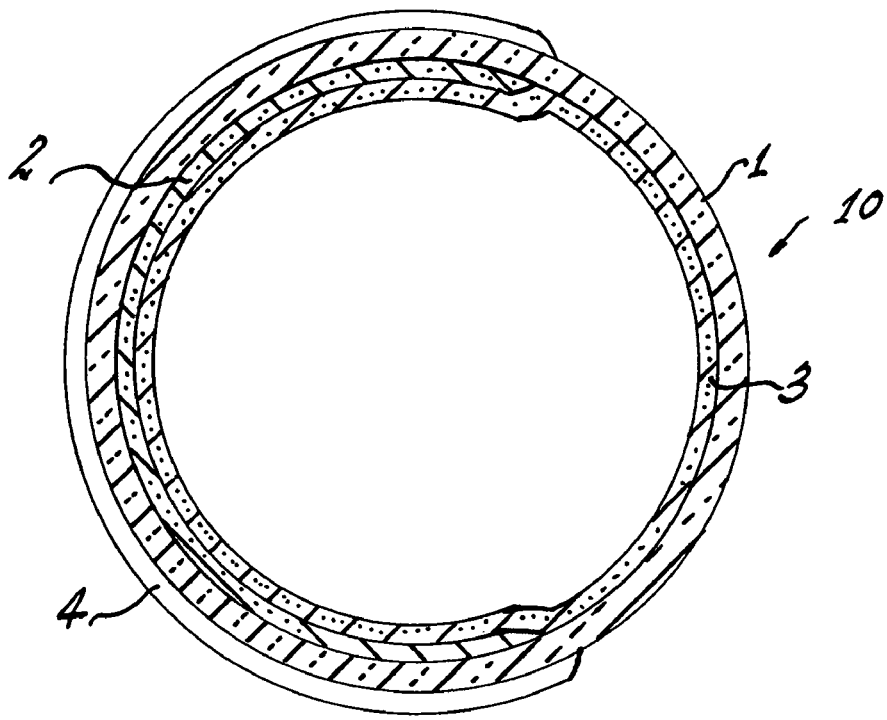
FIG. 2 is a similar view of a lamp according to an embodiment of the invention.

FIG. 2 is a similar view, albeit of an embodiment of the invention. Therein the lamp 10 includes a layer 4 of photocatalytic material deposited on the outside surface of the envelope 1. As used herein the term photocatalytic material refers to a material exhibiting photocatalysis, that is, the acceleration of a chemical reaction by radiant energy (as light) acting either directly or by exciting a substance that in turn catalyzes the main reaction. Layer 4 preferably is anatase $TiO_2$ having a thickness of 0.1 to 10 μm, preferably, 0.1 to 1.0 μm. The anatase form of $TiO_2$ is known to have the highest overall photocatalytic activity.

It is noted that U.S. Pat. No. 3,987,331, cited above, discloses the use of $TiO_2$ as a reflective layer on the interior of an envelope; however, there can be no photocatalytic effect from $TiO_2$ unless it is exposed to the atmosphere.

Other materials that can effectively be used to provide a photocatalytic effect are $ZnO$, $Bi_2O_3$, $WO_3$, $SrTiO_3$, $CeO_2$, $Fe_2O_3$, and mixtures thereof. Additionally, the inclusion of minor amounts, for example, as much as 1-2 percent by weight, of transition metals (e.g., Pt, Pd, Ru, Rh, Ir, or Os) can be helpful, as they are known to occasionally increase photocatalytic activity.

To determine the efficacy of the invention, a 160W VHR T12 tanning reflector lamp was examined spectroradiometrically. Irradiance measurements were made with the reflector-coated side of the lamp facing either away from or toward the detector. The lamp was mounted horizontally and perpendicular to the optical axis of the input sphere of the spectroradiometer, with the position of the lamp adjusted so as to place the center of the lamp on the optical axis of the sphere. Distance was set to 10.0 cm from the bulb centerline to the limiting aperture of the input sphere. An opaque block with a 2.5 inch circular clear aperture was placed at the lamp's surface, not touching the lamp, to prevent out-of-path stray light from affecting the measurement.

Figure 3:
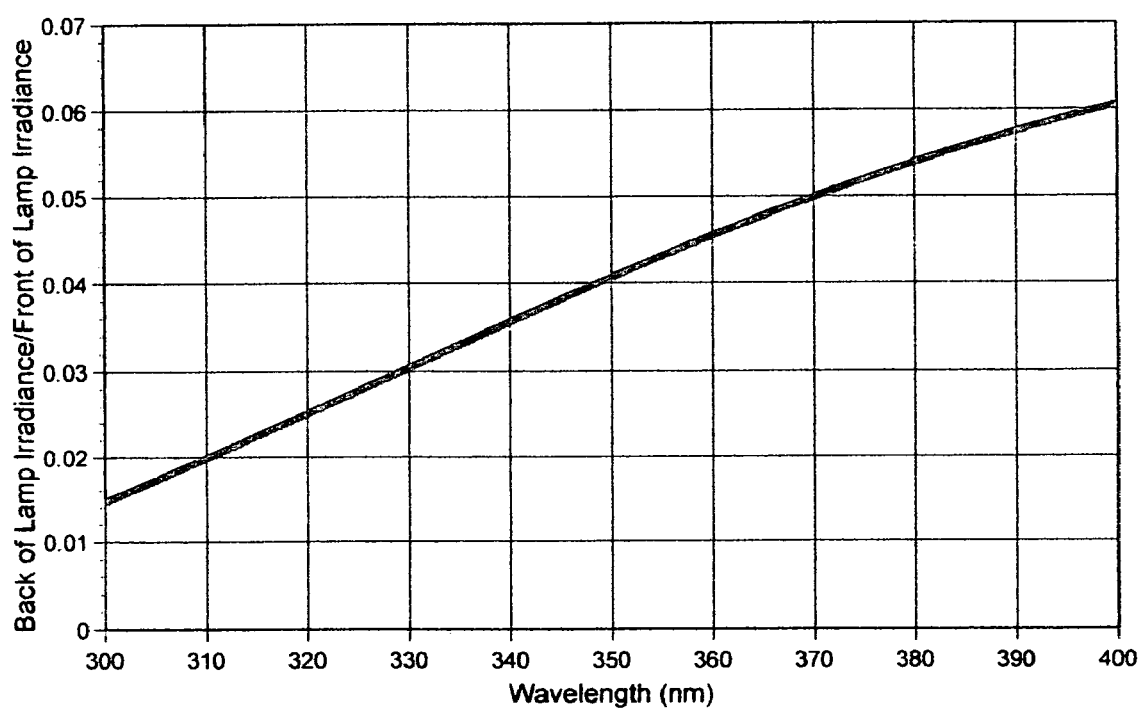
FIG. 3 is a graph of the ratio of emitted frequencies from the reflector side of the lamp versus the window side of the lamp.
Figure 4:
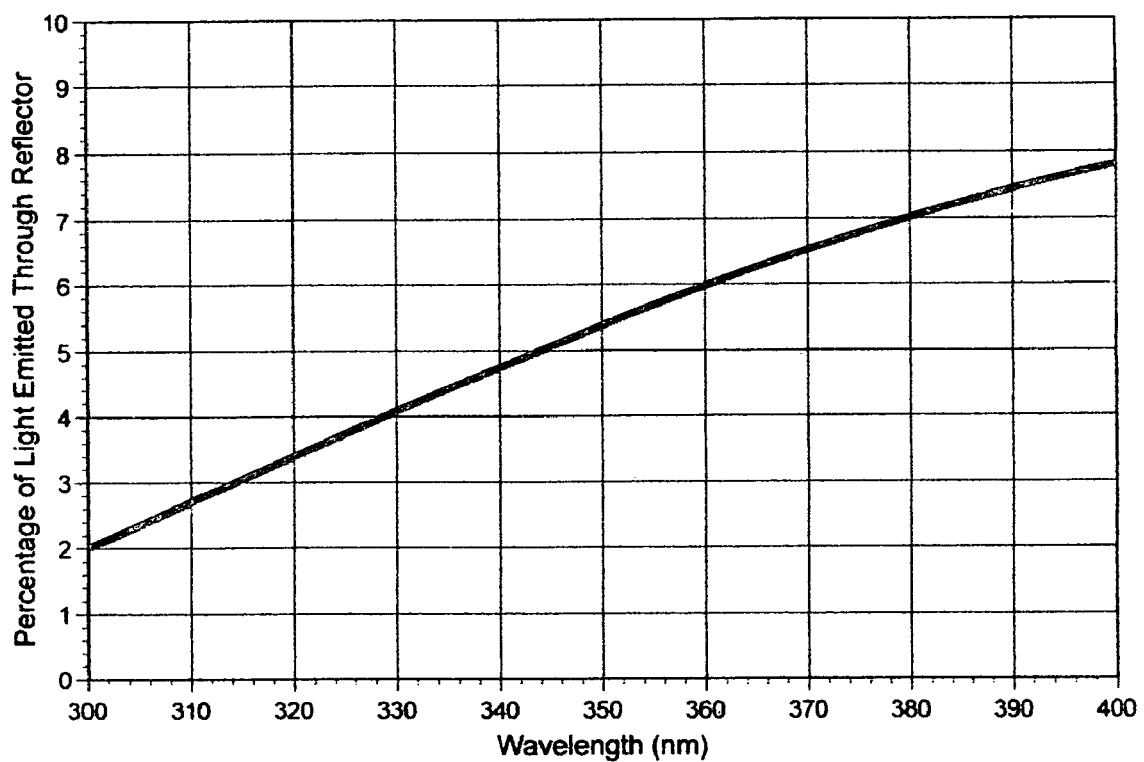
FIG. 4 is a graph of the percentage of emitted radiation through the reflector as function of frequency.

The ratio of the irradiance measured with the back (reflector side) of the lamp facing the detector to that measured with the front (non-reflector side) of the lamp facing the detector is plotted, for wavelengths ranging between 300 and 400 nm, in FIG. 3. The ratio increases approximately linearly from about 0.015 to 0.06 as the wavelength is increased from 300 nm to 400 nm, with the average ratio being about 0.04. The percentage of light emitted through the reflector is plotted similarly in FIG. 4, ranging from about 2% to about 8%. i.e., on average, about 5% of the light emitted by the lamp at wavelengths ranging between 300 and 400 nm is emitted through the reflector.

This is radiation that was previously unused.

Figure 5:
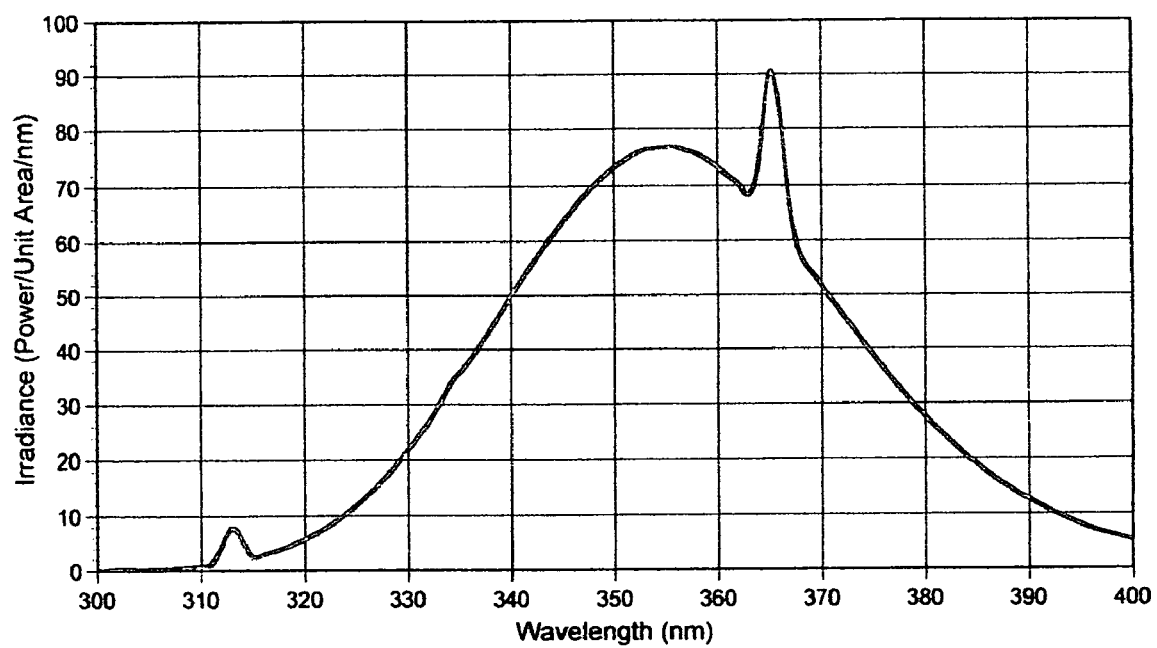
FIG. 5 is a graph of the irradiance of the radiation emitted through the reflector.
Figure 6:
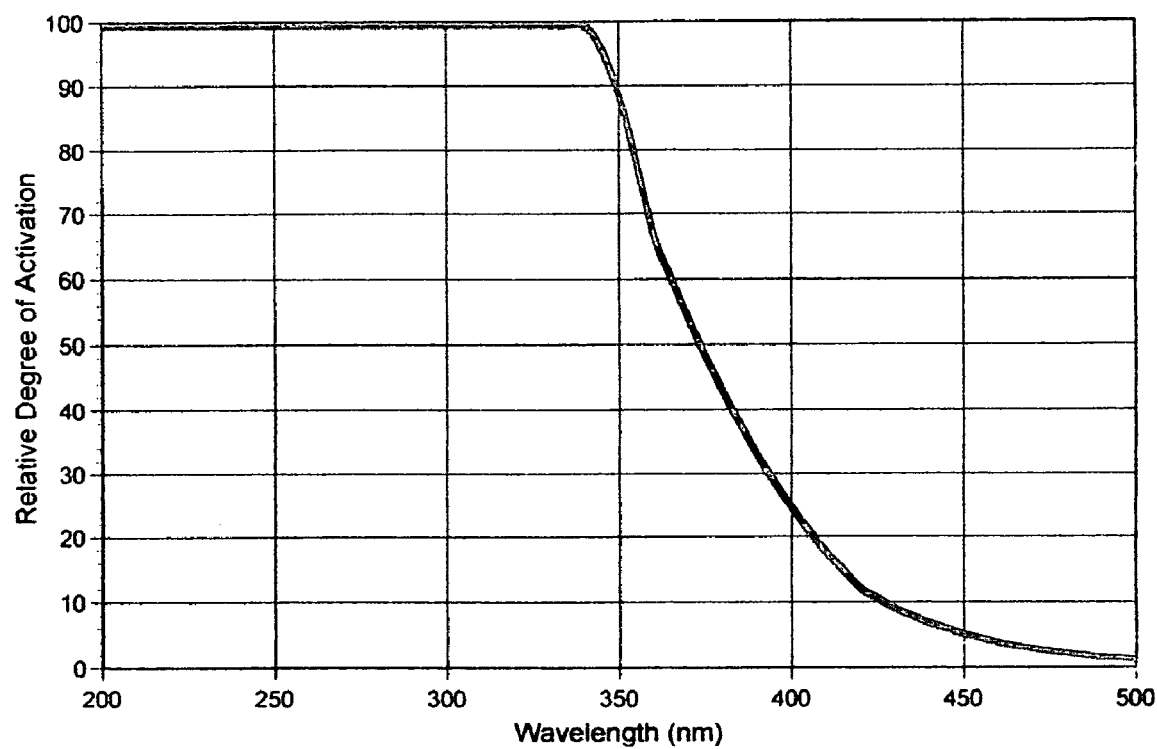
FIG. 6 is a graph of the relative degree of activation of the photocatalyst.

The irradiance (arbitrary scale) measured with the reflectorized side of the lamp (described above) facing the detector is plotted in FIG. 5 for wavelengths ranging between 300 and 400 nm. As shown, the irradiance reaches a maximum at wavelengths between 350-360 nm. The relative degree of photocatalytic activation of anatase $TiO_2$ is similarly plotted in FIG. 6 (for wavelengths between 200 and 500 nm). The efficacy of UV radiation to effect the photocatalytic activity of $TiO_2$ also rapidly increases as the wavelength of the incident light decreases to about 350 nm. Using the $TiO_2$ photocatalytic activation curve as a weighting factor, it is calculated that the power density of the lamp that is effective for the activation of a $TiO_2$ coating deposited upon the reflectorized side of the T12 suntan lamp is on the order of 1 mW/cm$^2$, more than enough to activate the photocatalyst.

The odor neutralizing fluorescent sunlamp described above, with a film of photocatalytic material deposited upon the portion of the outer surface of the lamp envelope that is coextensive with the internal reflector, may possess additional beneficial properties as a result of the presence of the photocatalyst. Specifically, the operating lamp may also be expected to possess antibacterial and antifungal properties, and the portion of the lamp upon which the photocatalyst is deposited will possess a self-cleaning characteristic. Of course, the same properties would be obtained, albeit to a reduced extent, if the photocatalyst were deposited upon less than 100% of the portion of the outer surface of the lamp envelope that is coextensive with the internal reflector.

While there have been shown and described what are present considered to be the preferred embodiments of the invention, it will be apparent to those skilled in the art that various changes and modifications can be made herein without departing from the scope of the invention as defined by the appended claims.

What is claimed is:

1. In a fluorescent sun tanning lamp providing substantial radiation between 320-400 nm and having:

a glass envelope;

an ultra-violet light reflecting coating covering at least 180° of an inside surface of said envelope; and a phosphor layer covering substantially 360° of said inside surface of said envelope, including overlying said ultra-violet reflecting coating, the improvement comprising:

a photocatalytic material on an outside surface of said envelope, said photocatalytic material being coextensive with said ultra-violet light reflecting coating.

2. The fluorescent tanning lamp of claim 1 wherein said photocatalytic material is selected from the group consisting essentially of $TiO_2$, ZnO, $Bi_2O_3$, $WO_3$, $SrTiO_3$, $CeO_2$, $Fe_2O_3$, and mixtures thereof.

3. The fluorescent tanning lamp of claim 2 wherein said photocatalytic material contains an amount of a transition metal sufficient to enhance the effect of said photocatalytic material.

4. The fluorescent tanning lamp of claim 2 wherein said photocatalytic material is anatase $TiO_2$.

5. A fluorescent lamp comprising:
   a glass envelope containing an arc generating and sustaining medium;
   a phosphor within said lamp that emits radiation in response to excitation by said arc, a substantial amount of said radiation being in the range of 320-400 nm;
   a reflective layer on a portion of an inside surface of said fluorescent lamp that reflects substantially all of said emitted radiation through a window in a front surface of said envelope and a minor fraction of said radiation through a portion of said lamp opposite said window; and
   a photocatalytic material on said portion of said lamp opposite said window.

6. The fluorescent lamp of claim 5 wherein said photocatalytic material is selected from the group consisting essentially of $TiO_2$, ZnO, $Bi_2O_3$, $WO_3$, $SrTiO_3$, $CeO_2$, $Fe_2O_3$, and mixtures thereof.

7. The fluorescent lamp of claim 6 wherein said photocatalytic material contains an amount of a transition metal sufficient to enhance the effect of said photocatalytic material.

8. The fluorescent lamp of claim 6 wherein said photocatalytic material is anatase $TiO_2$.

9. A method of deodorizing a tanning booth comprising the steps of:
   a.) installing in said booth a fluorescent lamp that generates ultra-violet radiation in the range of 320-400 nm and emits a substantial amount of said ultra-violet radiation in a first direction and a minor amount in a second direction substantially opposite said first direction, said lamp containing on an outer surface thereof a photocatalytic material responsive to said minor amount of said ultra-violet radiation emitted in said second direction: and
   b.) energizing said lamp.

* * * * *